United States Patent [19]
DeFlorio et al.

[11] Patent Number: 5,912,380
[45] Date of Patent: Jun. 15, 1999

[54] METHOXYCINNAMYLOXY SALYCILATE AND PREPARATION THEREOF

[75] Inventors: Victor DeFlorio, Cranford, N.J.; Joseph Michael Corey, Waterbury; Anthony Vargas, Monroe, both of Conn.

[73] Assignee: Elizabeth Arden Co., Division of Conopco, Inc., New York, N.Y.

[21] Appl. No.: 09/048,733

[22] Filed: Mar. 26, 1998

[51] Int. Cl.⁶ .................................................. C07C 69/88
[52] U.S. Cl. ................................................................ 560/71
[58] Field of Search ................................................ 560/71

[56] References Cited

U.S. PATENT DOCUMENTS 2,116,347  5/1938  Grether et al. .

FOREIGN PATENT DOCUMENTS 0676194  11/1995  European Pat. Off. .

*Primary Examiner*—Paul J. Killos
*Attorney, Agent, or Firm*—Rimma Mitelman

[57] ABSTRACT

Methoxycinnamyloxy salicylate and method of its preparation is described. Methoxycinnamyloxy salicylate is useful in skin care compositions, to improve the appearance of the skin.

2 Claims, No Drawings

METHOXYCINNAMYLOXY SALYCILATE AND PREPARATION THEREOF

FIELD OF THE INVENTION

The invention relates to a new compound, methoxycinnamyloxy salicylate, and a method for its preparation.

BACKGROUND OF THE INVENTION

The compound of the present invention is a non-ring esterified salicylic acid compound, where salicylic acid is bonded via an ester linkage to ferulic acid. Ferulic acid is also known as methoxycinnamic acid.

Several patents describe esters of salicylic acids. See for instance U.S. Pat. No. 2,116,347 (Grether et al.) and EP 0676194 (Roussel Uclaf). The esters described for the most esters are alkyl esters of salicylic acid. Roussel Uclaf also mentions isopropylbenzyl salicylate. Neither Grether et al. nor Roussel Uclaf describes the ester of the present invention.

Grether's salicyloxy carboxylic acid esters further differ from the inventive compound in at least in that the Grether's compounds contain an ester group in place of a terminal carboxy group of the inventive compounds. Thus, the Grether compounds contain two ester bonds, whereas the inventive compound contains only one ester bond. The inventive compounds cannot be obtained by merely hydrolyzing the ester obtained by the Grether process, since the first ester linkage would be hydrolyzed first to produce salicylic acid and ferulic acid.

SUMMARY OF THE INVENTION

The present invention includes a compound of Formula I:

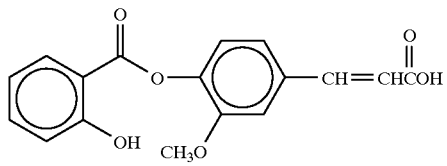

The present invention also includes a process of making the novel compound.

The inventive compounds are useful in skin care cosmetic compositions, to improve the appearance of the skin.

DETAILED DESCRIPTION OF THE INVENTION

Except in the operating and comparative examples, or where otherwise explicitly indicated, all numbers in this description indicating amounts of material, ratios, or conditions of reaction, physical properties of materials and/or use are to be understood as modified by the word "about." All amounts are by weight, unless otherwise specified.

The terms "methoxycinnamyloxy salicylate" and "ferulyl salicylate" are used interchangeably herein.

The compound according to the present invention has the general Formula I:

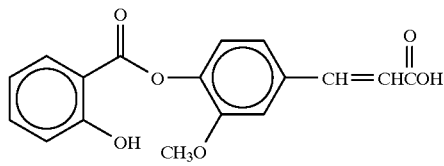

The inventive process of making the compound of Formula I includes at least two steps:
(a) preparing a salicylic acid halide by reacting salicylic acid with thionyl halide or oxalyl halide; and
(b) reacting the salicylic acid halide with ferulic acid, to obtain the inventive compound of Formula I.

In the first step, salicylic acid is mixed with thionyl (or oxalyl) halide, most preferably chloride, (molar ratio in the general range of from 1:1 to 2:1) in an anhydrous, typically non-polar, solvent, in the presence of pyridine catalyst, at a temperature of from 20 to 45° C. for 0.5–2 hours. At the end of this reaction, salicylic acid chloride is obtained. Optionally, the solvent is distilled at least partially.

Subsequently, ferulic acid is dissolved in a dry solvent (e.g. dry acetone, toluene, THF) and pyridine is added to this solution (1 equivalent per 1 equivalent of salicylic acid halide). Salicylic acid chloride is added dropwise, with stirring, to this solution. The molar ratio of salicylic acid chloride to ferulic acid is typically in the range of from 1:1 to 1:2. The reaction is conducted typically 40–45° C. for several hours, before being heated to reflux for 3 hours, and the completion is monitored by TLC.

Subsequently, the solvent is removed and the product is isolated by extraction and purified by column chromatography and recrystallization. The product is a white powder.

The following specific examples further illustrate the invention, but the invention is not limited thereto.

EXAMPLE 1

Methods and Materials

Proton magnetic resonance spectra were recorded on a Bruker AC 200 model spectrophotometer. Chemical shifts are reported in parts per million from teramethylsilane as an internal standard. Spin multiplicities are indicated as follows: s (singlet), d (doublet), t (triplet), q (quartet), m (multiplet) and br (broad). The deuterated NMR solvents contain 99.0–99.8% deuterium in the indicated position, and were purchased from Cambridge Isotopic Laboratories.

Gas chromatography (GC) was performed using a Hewlett-Packard 5890 Series II gas chromatograph with an HP 7673 injector controlled by the Hewlett-Packard Chem-Station software. The Hewlett-Packard HP-1 column used was 25 M×0.22 mm with a 0.33 um coating of cross-linked methyl silicone. The parameters were as follows:
Inj. temp.=290° C., det. temp.=290° C., initial oven temp.=50° C., initial time=5 min., rate=25° C./min., final oven temp.=290° C. Samples were analyzed as trimethyl silyl ethers/esters.

Gas chromatography/mass spectrometry was performed on a Hewlett-Packard 5890 Series II gas chromatograph in conjunction with a Finnigan MAT ITD 800 ion trap detector. The 25 M×0.32 mm HP-5 column had a 0.52 um coating of 5% cross-linked phenyl methyl silicone.

Differential Scanning Calorimetry experiments were run on a Dupont DSC with a 2910 cell base and a 2100 thermal analyst. Samples of approximately 1 mg were accurately weighed into aluminum pans which were than hermetically sealed. After equilibration at 30° C., the samples were heated at a rate of 5° C./minute.

All solvents were reagent grade and were used as received. All reagents were purchased from the Aldrich or Sigma Chemical Companies and were used as received.

Step 1

Into a clean, dry 250 mL round bottomed flask were charged 5.0 g (36 mmoles) of salicylic acid, 100 mLs of anhydrous toluene and 4–5 drops of pyridine catalyst. The flask was equipped with a stir bar, addition funnel and nitrogen bubbler. Into the addition funnel were charged 4.7 g (40 mmoles) of thionyl chloride in 20–25 mLs of anhydrous toluene. The thionyl chloride solution was added to the reaction flask dropwise under ambient conditions. When the addition was complete, the reaction stirred at 40–45° C. for several hours before any excess thionyl chloride and some of the toluene were removed under vacuum.

Step 2

Into a clean, dry 500 mL round bottomed flask were charged 7.0 g (36 mmoles) of ferulic acid, 200 mLs of anhydrous toluene and 3.4 g (40 mmoles) of pyridine. The flask was equipped with a stir bar, addition funnel and nitrogen bubbler. Into the addition funnel was added the salicyloyl chloride solution. The salicyloyl chloride solution was added to the reaction flask dropwise under ambient conditions. When the addition was complete, the reaction stirred at 40–45° C. for several hours before being heated to reflux for 3 hours before the heat was removed and the reaction continued to stir under ambient conditions overnight.

The reaction mixture was filtered under vacuum to remove the brown precipitate formed during the reaction. The toluene filtrate was concentrate under vacuum to yield 5.2 g of yellow solid which was 52% methoxycinnamyloxy salicylate by gas chromatography and gas chromatography/mass spectrometry. 2.4 g of the product were purified by silica gel column chromatography to yield 600 mg of pure methoxycinnamyloxy salicylate (a.k.a. ferulyl salicylate) as a fine white powder.

$^1$H NMR(200 MHz, CdCl3): d 8.0 (d, 1H), 7.6(m, 2H), 7.0(m, 2H), 6.5 (d, 1H), 3.9 (s, 3H)

GC (Retention time): 15.9 minutes

DSC: Onset Temperature(°C.): 192 m/z (GC/MS): 531 [M+H] $^+_{(3 \times TMS)}$

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A compound of Formula I:

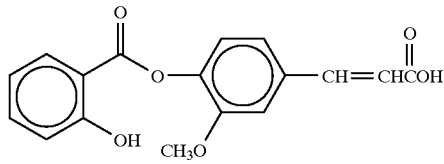

2. A process of making a compound according to claim 1, wherein the process comprises the steps of:

(a) preparing a salicylic acid halide by reacting salicylic acid with thionyl halide or oxalyl halide; and (b) reacting the salicylic acid halide with ferulic acid, to obtain the inventive compound of Formula I.

* * * * *